(12) United States Patent
Dai et al.

(10) Patent No.: US 10,926,088 B2
(45) Date of Patent: Feb. 23, 2021

(54) PORTABLE ELECTRONIC PULSE STIMULATOR WITH INTEGRATED ULTRASOUND AND TENS/EMS

(71) Applicant: JKH Health Co., Ltd., Shenzhen (CN)

(72) Inventors: Quanqin Dai, Diamond Bar, CA (US); Pu Jiang, Shenzhen (CN)

(73) Assignee: JKH Health Co., Ltd., Shenzhen (CN)

( * ) Notice: Subject to any disclaimer, the term of this patent is extended or adjusted under 35 U.S.C. 154(b) by 314 days.

(21) Appl. No.: 16/016,119

(22) Filed: Jun. 22, 2018

(65) Prior Publication Data

US 2018/0369583 A1 Dec. 27, 2018

(30) Foreign Application Priority Data

Jun. 27, 2017 (CN) .............................. 107320845A

(51) Int. Cl.
*A61N 7/00* (2006.01)
*A61N 1/36* (2006.01)
*A61F 7/00* (2006.01)
*A61N 1/04* (2006.01)

(52) U.S. Cl.
CPC .......... *A61N 1/36021* (2013.01); *A61F 7/007* (2013.01); *A61N 1/0456* (2013.01); *A61N 7/00* (2013.01); *A61N 1/0452* (2013.01); *A61N 1/0476* (2013.01); *A61N 1/0492* (2013.01); *A61N 1/36003* (2013.01)

(58) Field of Classification Search
None
See application file for complete search history.

(56) References Cited

U.S. PATENT DOCUMENTS 8,620,438 B1* 12/2013 Wijting ................ A61N 1/0452
607/48
2016/0350509 A1* 12/2016 Sharma .................... A61N 7/00

* cited by examiner

*Primary Examiner* — Joel F Brutus
(74) *Attorney, Agent, or Firm* — Karthik Murthy; Murthy Patent Law PLLC

(57) ABSTRACT

A portable electronic pulse stimulator with integrated Ultrasound and TENS/EMS includes a unit and a electrode pad. The unit includes IC board and housing; the IC board has an Ultrasound output module and a TENS/EMS output module; The electrode pad has Ultrasound therapy head and TENS/EMS electrode. The invention can add the heating function and the heating intensity can be adjusted if needed. At the same time, this invention can add the remote control function, meaning the electronic pulse stimulator can both receive and send data. The unit can work independently and is portable.

12 Claims, 8 Drawing Sheets

PORTABLE ELECTRONIC PULSE STIMULATOR WITH INTEGRATED ULTRASOUND AND TENS/EMS

BACKGROUND

The existing TENS/EMS (Transcutaneous Electrical Nerve Stimulation/Electrical Muscle Stimulation) electronic pulse stimulator usually consists of a control unit and sticky electrode pads attached to the skin, and the unit is connected to the electrode pads through the lead wires. While using, the user sticks the electrode pads to the skin of the body area with pain. The pain relief is achieved by generating the output pulse from the unit to the body area with pain. However, the TENS/EMS electronic pulse stimulator can't generate obvious physical therapy effect on the pain in the deep muscle, which limits the physical therapy effect.

SUMMARY

On the other hand, the Ultrasound could penetrate into the deep muscle and achieve the deep muscle therapy, its effect is remarkable. However, now Ultrasound electronic pulse stimulator on the market always be large in size, not portable, with high-voltage (e.g. 100-220 V) power supply, and expensive.

With the improvement of lifestyle over time, people are paying more and more attention to the idea of healthy life. If there was an electronic pulse stimulator with small size, portability and integrated function of Ultrasound and TENS/EMS, it would be favored by people. Therefore, we need to make further improvements.

TECHNICAL FIELD

The invention relates to a portable electronic pulse stimulator with integrated Ultrasound and TENS/EMS. In particular, it is a portable electronic pulse stimulator with both Ultrasound and TENS/EMS, which belongs to the physiotherapy field.

DETAILED DESCRIPTION

Figure 1:
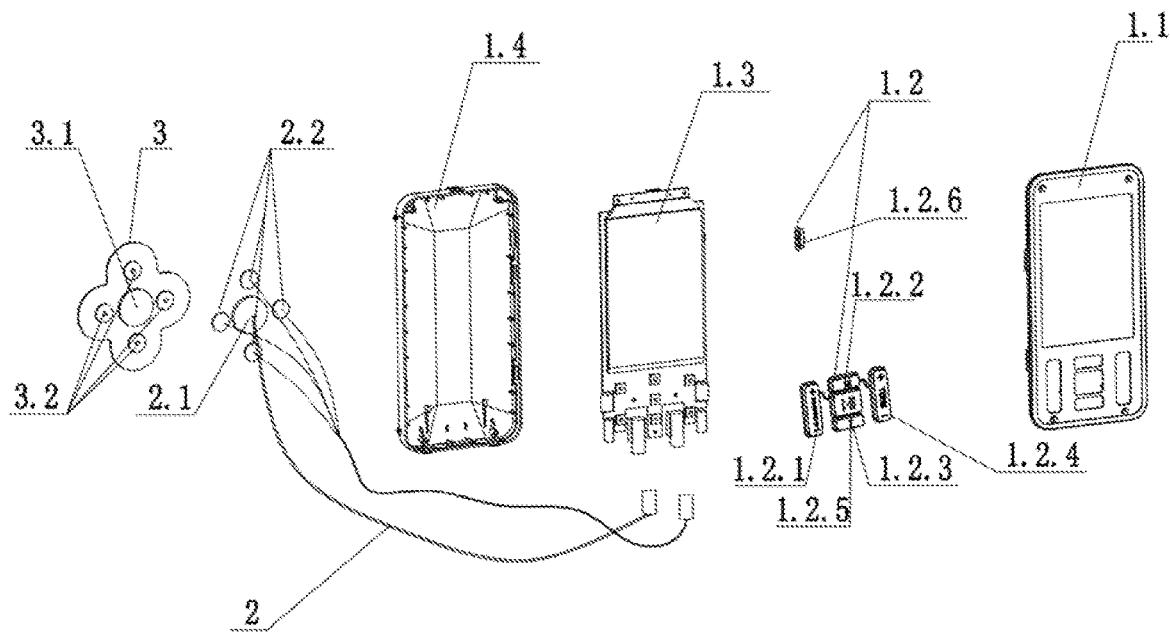
FIG. 1 is the decomposed structure to illustrate the wire connection (with the same one-piece electrode pad) for the 1st invention.

The invention aims to provide a portable electronic pulse stimulator which is small in size, easy to carry and has both TENS/EMS and Ultrasound therapy functions. Its TENS/EMS and Ultrasound therapy functions could both be used together or independently to overcome the shortcomings of the existing technology.

In order to achieve the above purpose, the invention provides a portable electronic pulse stimulator with integrated Ultrasound and TENS/EMS functions, including the unit and electrode pad. The above unit and electrode pad are electrically connected to each other, and have the following characteristics:

The above unit includes IC board and housing; the above IC board has both output modules of Ultrasound and TENS/EMS; the above electrode pad has both Ultrasound therapy head and TENS/EMS electrode.

The above unit could be electrically connected by the lead wire. The above lead wire includes the Ultrasound lead wire and the TENS/EMS lead wire. One end of the above lead wire is connected to the Ultrasound therapy head and conductive connector. The above Ultrasound therapy head and conductive connector are fixedly connected to the electrode pad. The other end of the above lead wire is connected to the output port of the IC board. The above unit and electrode pad could also be directly connected without wires. The unit and the electrode pad are electrically connected to each other through the conductive connectors and Ultrasound therapy head.

The above Ultrasound therapy head and conductive connector could be on the same electrode pad; the above electrode pad includes Ultrasound therapy head, sticky gel, conductive layer, non-conductive layer and conductive connectors.

The above Ultrasound therapy head and TENS/EMS electrode could be separately on two electrode pads; the above first electrode pad includes Ultrasound therapy head; the above second electrode pad includes sticky gel, conductive layer, non-conductive layer and conductive connectors.

The above unit includes batteries and function keys; the above batteries could be the rechargeable battery or non-rechargeable battery; the above function keys includes power on/off key, Ultrasound key, and TENS/EMS key.

Optionally, the above IC board could also include a temperature control module. The above electrode pad also could include the heating layer. The above temperature control module is connected to the heating layer of the electrode pad. The above heating layer is placed between the non-conductive layer and the pulse conductive layer.

Optionally, the above IC board also includes the signal receiving/transmitting module. The above unit could achieve the remote manipulation by the remote (e.g. Bluetooth, radio wave and WIFI).

In the invention, the unit can realize the integrated Ultrasound and/or TENS/EMS function through one or more electrode pads. The electronic pulse stimulator not only could use the Ultrasound and TENS/EMS function together at the same time, but also could use either of the Ultrasound and TENS/EMS functions separately. Except the lead wire connection, the unit and the electrode pad could also be wireless connected through the connectors (e.g. snap fastener) and the Ultrasound therapy head on the electrode pad.

The Ultrasound function of the invention does not need 100-220V AC power supply, so it can be realized by the built-in battery. The invention is portable.

The invention can add the heating function, and it's an optional function. The heating level could be adjusted according if needed. Meanwhile, it could also have the optional remote function, which means the electronic pulse stimulator could both accept and send data. While the unit and electrode pad are used on the body area where the user can't easily reach, such as the lower back, we could use the remote (e.g. Bluetooth and radio wave) to properly solve the inconvenient operation problem. In addition to the remote operation, the unit could work independently.

Figure 2:
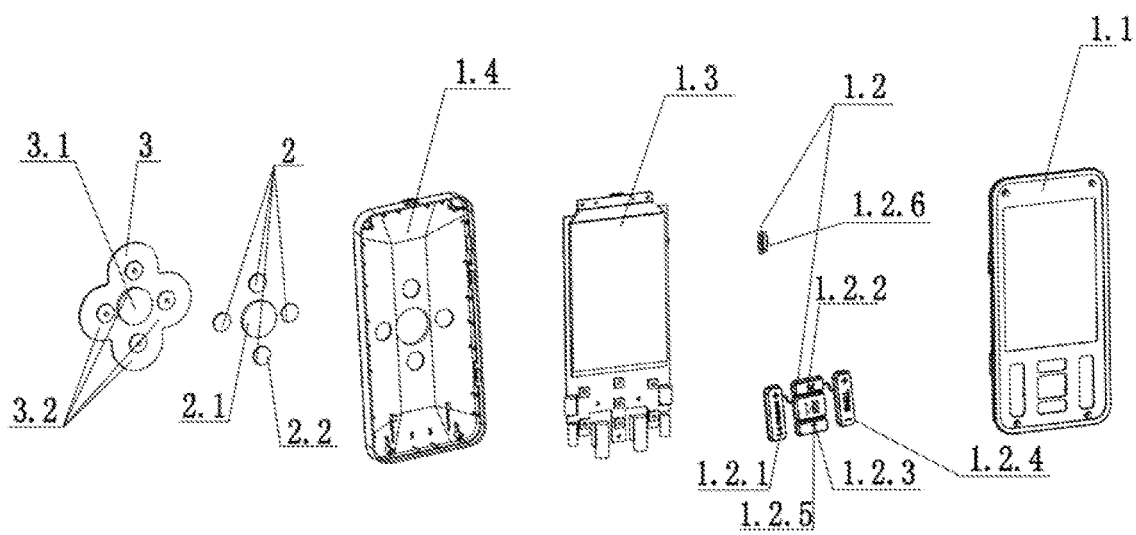
FIG. 2 is the decomposed structure to illustrate the wireless connection of the unit to the electrode pad by the connectors and head on the electrode pad for the 2nd invention.
Figure 3:
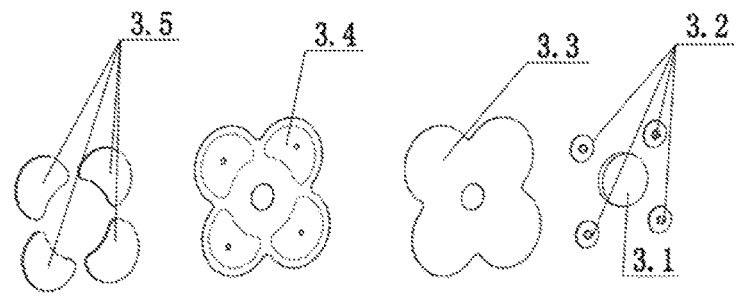
FIG. 3 is the decomposed structure to illustrate the electrode pad for the 1st and 2nd invention.
Figure 4:
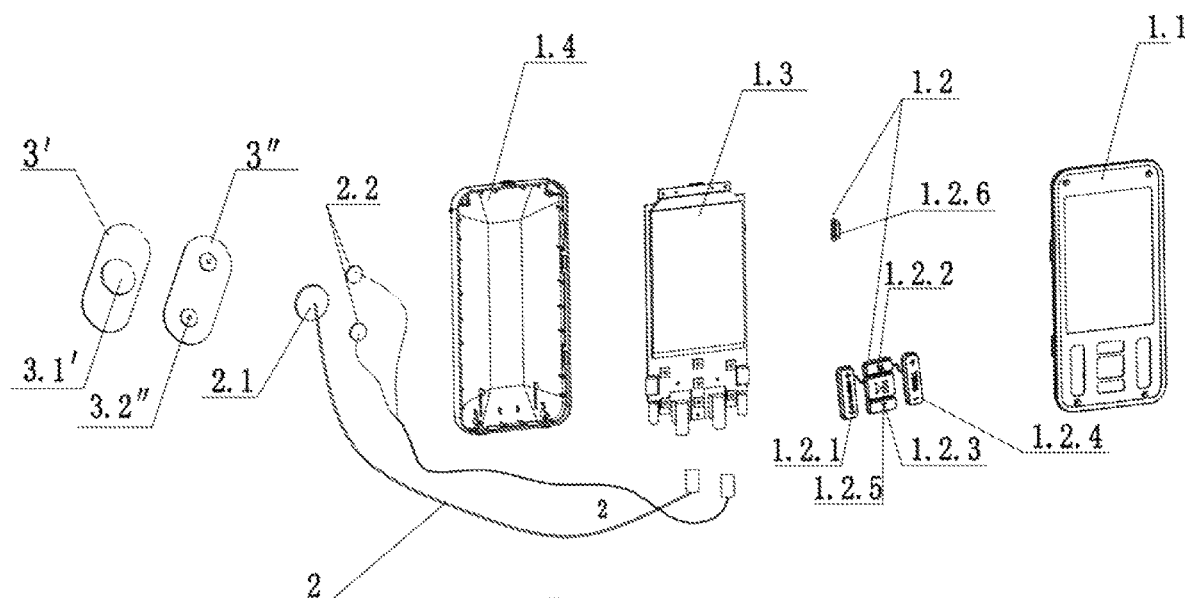
FIG. 4 is the decomposed structure to illustrate the wire connection (with two different pieces of electrode pads) for the 3rd invention.
Figure 5:
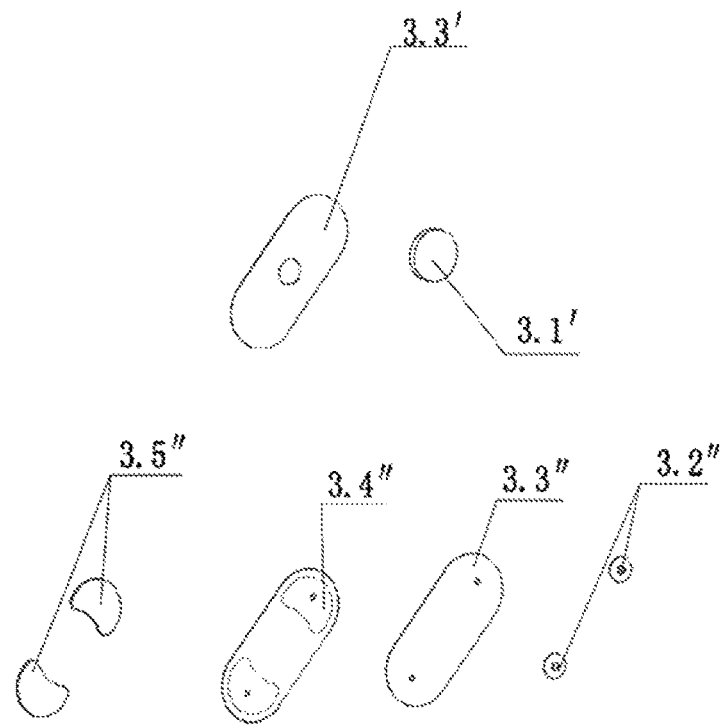
FIG. 5 is the decomposed structure to illustrate the electrode pad for the 3rd invention.
Figure 6:
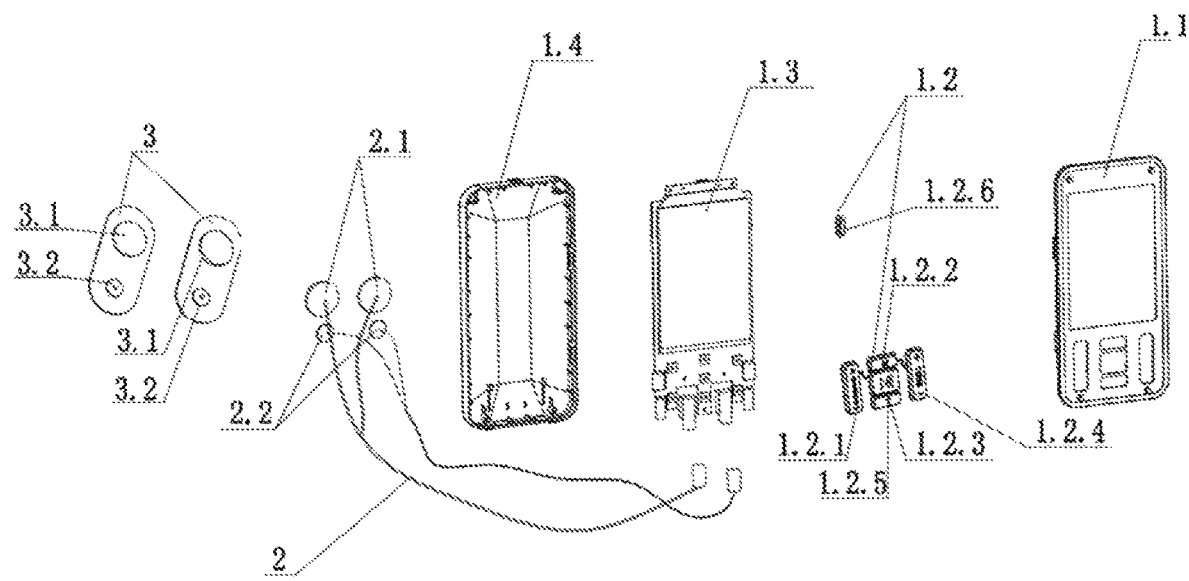
FIG. 6 is the decomposed structure to illustrate the wire connection (with two same pieces of electrode pads) for the 4th invention.
Figure 7:
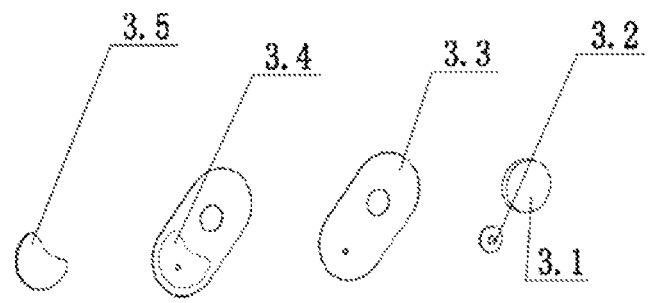
FIG. 7 is the decomposed structure to illustrate the electrode pads for the 4th invention.
Figure 8:
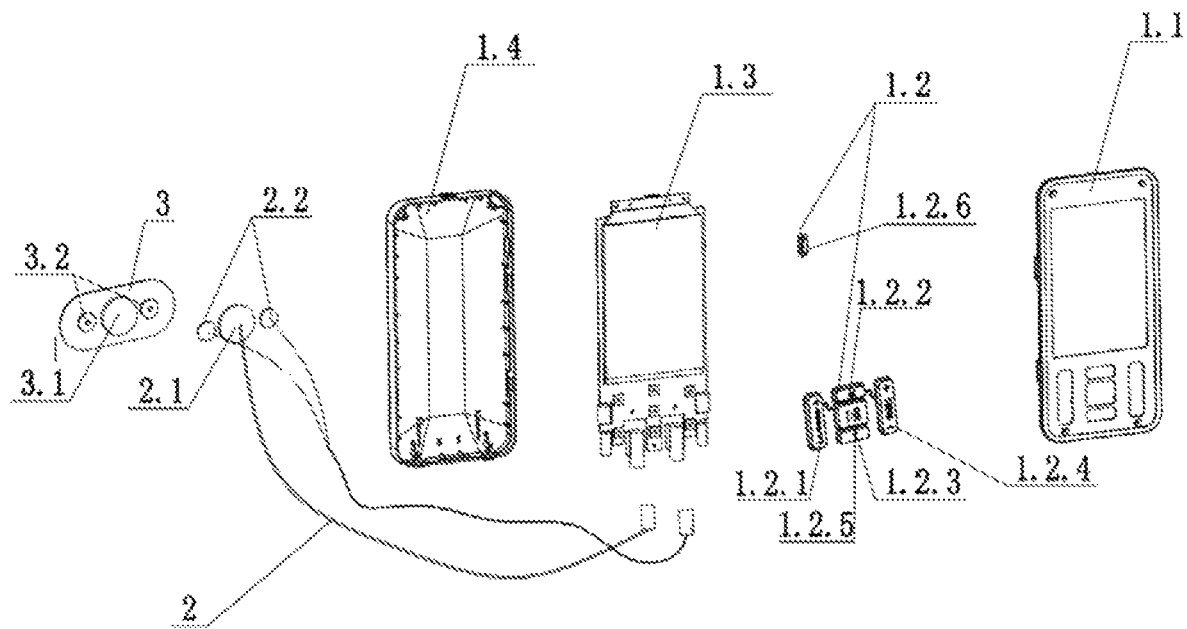
FIG. 8 is the decomposed structure to illustrate the wire connection (with the same one-piece electrode pad) for the 5th invention.
Figure 9:
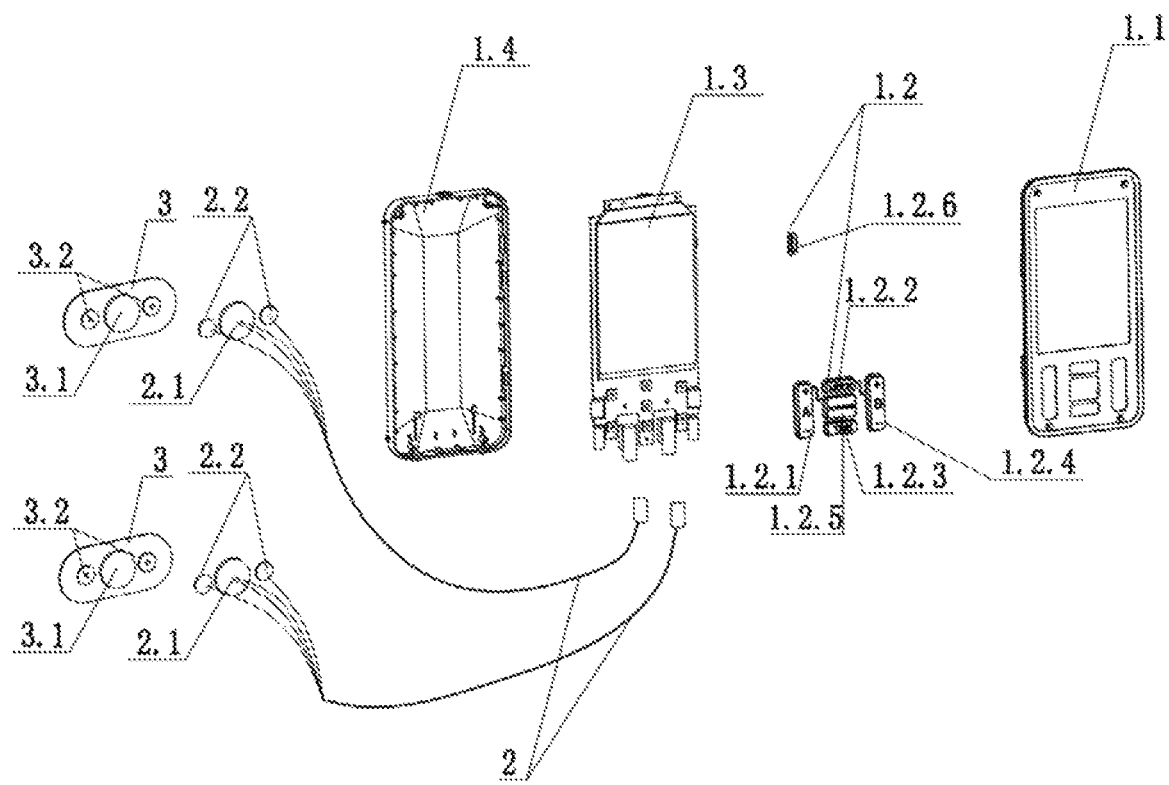
FIG. 9 is the decomposed structure to illustrate the wire connection (with two same pieces of electrode pads) for the 6th invention.
Figure 10:
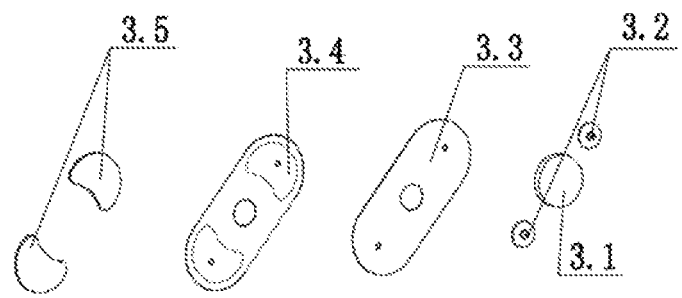
FIG. 10 is the decomposed structure to illustrate the electrode pads for the 5th and 6th invention.
Figure 11:
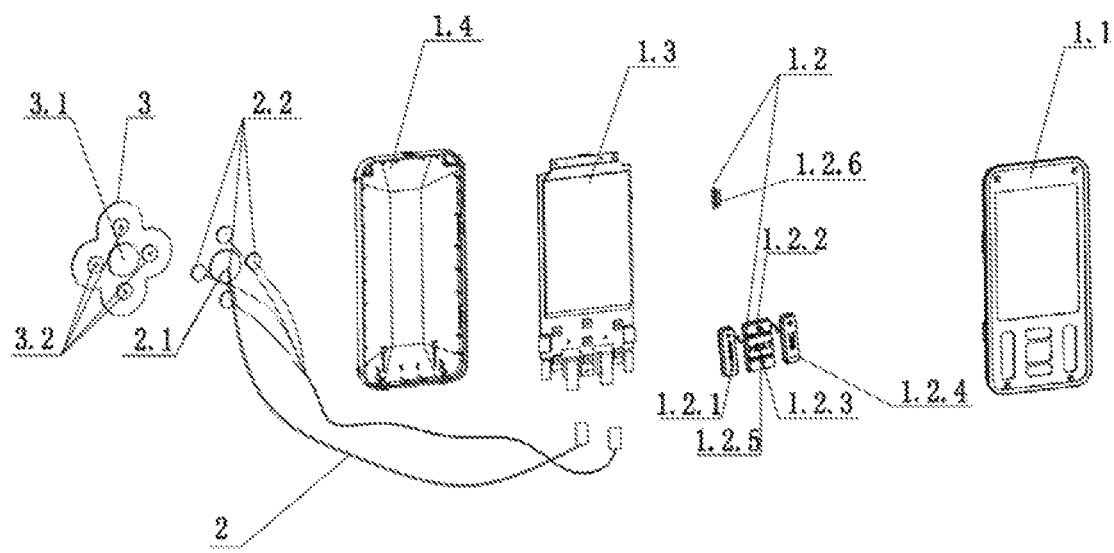
FIG. 11 is the decomposed structure to illustrate the addition of heating function for the 7th invention.
Figure 12:
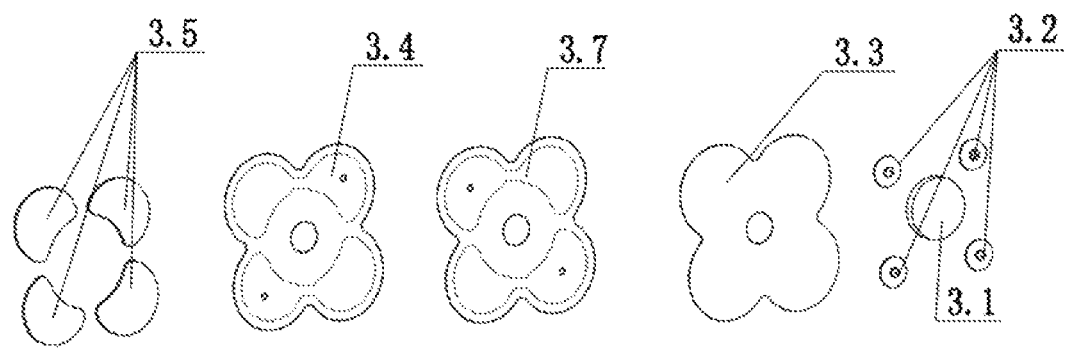
FIG. 12 is the decomposed structure to illustrate the electrode pad for the 7th invention.
Figure 13:
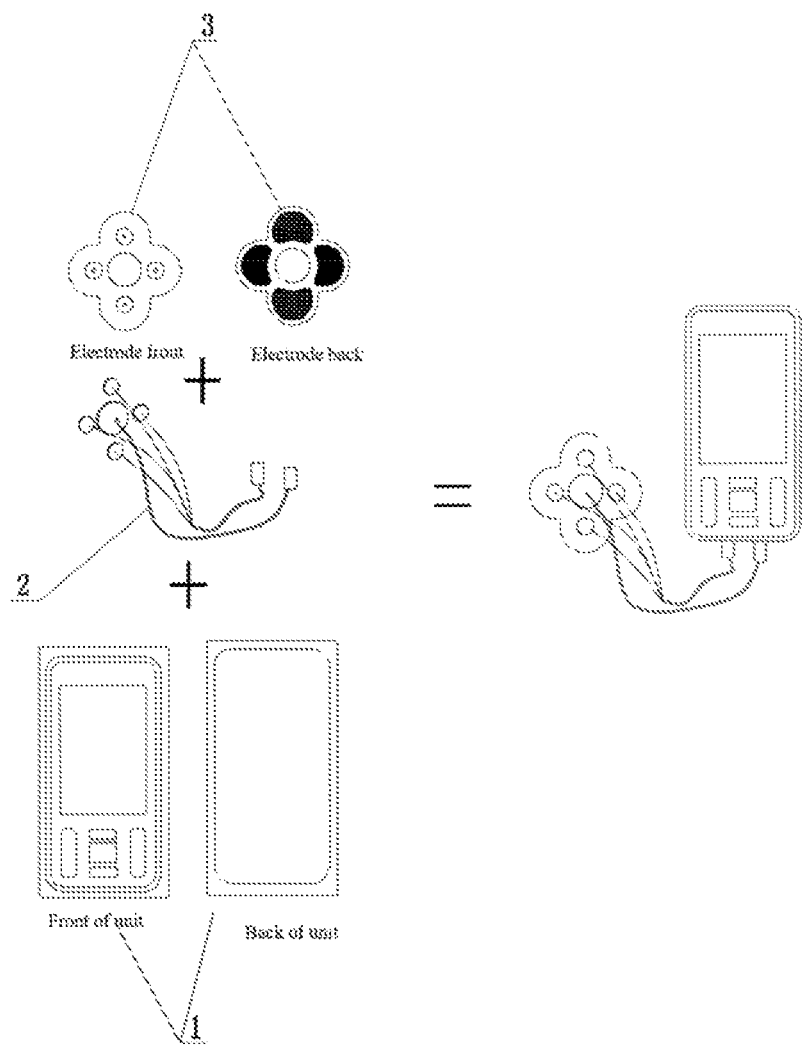
FIG. 13 is the assembly diagram to illustrate the wire connection of the unit and electrode pad.
Figure 14:
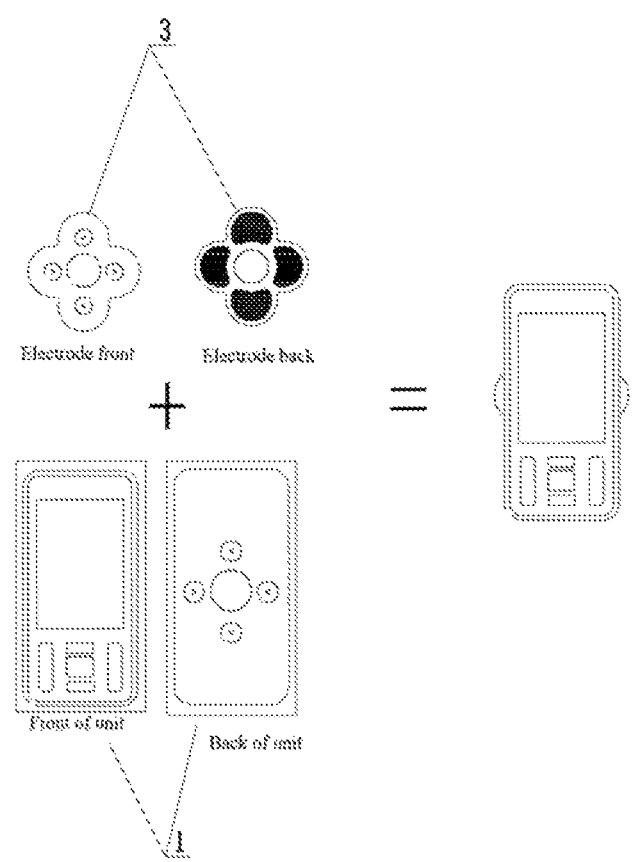
FIG. 14 is the assembly diagram to illustrate the wireless connection of the unit to the electrode pad by the connectors and head on the electrode pad.

As shown in FIG. 1 through FIG. 3: 1.1 and 1.4 are the housing of the unit, 1.2 are the function keys, 1.2.1 is the Ultrasound key, 1.2.2 is the mode adjustment key, 1.2.4 is the strength adjustment key, 1.2.5 is the pause key, 1.3 is the IC board, 2 are the lead wire, 2.1 is the Ultrasound therapy head on the lead wire, 2.2 are the electrode connectors on the lead wire, 3 is the electrode pad, 3.1 is the Ultrasound therapy head on the electrode pad, 3.2 is the TENS/EMS conductive connectors on the electrode pad, 3.3 is the non-conductive layer, 3.4 is the conductive layer, and 3.5 is the sticky gel.

See from FIG. 1 to FIG. 14, an electronic pulse stimulator combining Ultrasound and TENS/EMS, includes the unit 1 and electrode pad 3; the unit 1 and electrode pad 3 are connected electrically. The unit includes the IC board 1.3, housing 1.1 and 1.4; the IC board 1.3 possess the output modules for both Ultrasound and TENS/EMS; the electrode pad 3 possess the Ultrasound therapy head 3.1 and the TENS/EMS contact 3.2.

Further, the unit 1 and electrode pad 3 are connected electrically by the lead wire 2; the lead wire 2 could transfer both Ultrasound and TENS/EMS.

Further, 2.1 and 2.2 on one end of the lead wire 2, are respectively connect to the Ultrasound therapy head 3.1 and conductive connectors 3.2 on the electrode pad 3; the Ultrasound therapy head 3.1 and the conductive connectors 3.2 are fixed on the electrode pad 3; the other end of the lead wires connect to the output of the IC board 1.3.

Further, the unit 1 and the electrode pad 3 could be also wireless connected through the Ultrasound therapy head 2.1 and conductive connectors 2.2 that set on the IC board 1.3 or housing; 1.4, as well as the Ultrasound therapy head 3.1 and conductive connectors 3.2 that set on the electrode pad 3; the electrode pad 3 and unit 1 are connected electrically.

Further, the Ultrasound therapy head 3.1 and the TENS/EMS conductive connector 3.2 could be an the same electrode pad; the electrode pad 3 includes the Ultrasound therapy head 3.1, conductive connectors 3.2, non-conductive layer 3.3, conductive layer 3.4 and sticky gel 3.5.

Further, the Ultrasound therapy head 3.1 and the TENS/EMS conductive connector 3.2 could be also on two independent electrode pads; the 1st electrode pad 3' includes the Ultrasound therapy head 3.1; the 2nd electrode pad 3" includes the conductive connector 3.2", non-conductive layer 3.3", conductive layer 3.4" and sticky gel 3.5".

Further, the unit 1 includes battery and function keys 1.2; the battery is chargeable or non-rechargeable; function keys includes ON/OFF key 1.2.6, Ultrasound key 1.2.1, mode adjustment key 1.2.2, time adjustment key 1.2.3, TENS/EMS adjustment key 1.2.4, and/or pause key 1.2.5.

Further, the IC board 1.3 could also possess the temperature-adjusting module, and the electrode pad 3 could also possess the heating layer 3.7; the temperature-adjusting module and the heating layer 3.7 on the electrode pad 3 is connected electrically between the layer 33 and the conductive layer 3.4.

Further, the IC board 1.3 also includes the display and signal receiving and transmitting module; the unit could be operated by Bluetooth, radio wave or Wi-Fi remote manipulation.

The above shows and describes the basic principles, main features and advantages of this invention. The technical personnel in the field should understand that the invention is not limited by the above mentioned examples. The above-mentioned examples and illustration described here is only to illustrate the principles of the invention. In the premise of not deviating from the spirit and scope of the invention, there will be various changes and improvements in this invention. These changes and improvements will be fallen into scope of required protection of this invention. The scope of required protection should be defined by the appended claims and their equivalents.

What is claimed is:

1. A system of a portable Ultrasound and TENS/EMS electronic pulse stimulator including a unit and an electrode pad;
   wherein the unit and the electrode pad are electrically connected to each other by a lead wire or without wires, characterized in that the unit includes an IC board and a housing;
   Wherein the IC board has an Ultrasound output module and a TENS/EMS module;
   Wherein the electrode pad has an Ultrasound therapy head and a TENS/EMS electrode;
   wherein the unit and the electrode pad can be electrically connected by a lead wire;
   wherein one end of the lead wire is connected to the ultrasound head and the conductive connector of the electrode pad;
   wherein the Ultrasound therapy head and the conductive connector are fixedly connected to the electrode pad and/or the lead wire;
   wherein the other end of the wire is connected to the output port of the IC board;
   wherein the unit and the electrode pad can also be directly connected without wires;
   wherein the unit and the electrode pad are electrically connected to each other through the conductive connector and Ultrasound therapy head;
   wherein the conductive connector and the Ultrasound therapy head are on the electrode pad and/or the unit.

2. The system of claim 1, further comprising:
   wherein the Ultrasound therapy head and the TENS/EMS electrode can be attached in the same electrode pad;
   wherein the electrode pad includes the Ultrasound therapy head, conductive connector, non-conductive layer, conductive layer, and sticky gel.

3. The system of claim 2, further comprising:
wherein the IC board also includes a temperature adjustment module, and the electrode pad also includes a heating layer;
wherein the temperature adjustment module is electrically connected to the heating layer of the electrode pad;
wherein the heating layer is set between the non-conductive layer and conductive TENS/EMS layer.

4. The system of claim 1, further comprising:
wherein the Ultrasound therapy head and the TENS/EMS electrode can also be in two independent electrode pads;
wherein a first electrode pad includes an Ultrasound therapy head;
wherein a second electrode pad includes conductive connector, non-conductive layer, conductive layer, and sticky gel.

5. The system of claim 4, further comprising:
wherein the IC board also includes a signal receiving/transmitting module;
wherein the unit can be remotely operated through the signal receiving/transmitting module by Bluetooth, radio waves, or WIFI.

6. The system of claim 1, further comprising:
wherein the unit includes batteries and function keys;
wherein the batteries are rechargeable batteries or non-rechargeable batteries;
wherein the function keys include power on/off key, Ultrasound key, and TENS/EMS key.

7. A system of a portable Ultrasound and TENS/EMS electronic pulse stimulator including a unit and an electrode pad;
wherein the unit and the electrode pad are electrically connected to each other by a lead wire or without wires, characterized in that the unit includes an IC board and a housing;
wherein the IC board has an Ultrasound output module and a TENS/EMS module;
wherein the electrode pad has an Ultrasound therapy head and a TENS/EMS electrode;
wherein the unit and the electrode pad can be electrically connected by a lead wire;
wherein one end of the lead wire is connected to the ultrasound head and the conductive connector of the electrode pad;
wherein the Ultrasound therapy head and the conductive connector are fixedly connected to the electrode pad and/or the lead wire;
wherein the other end of the wire is connected to the output port of the IC board;
wherein the unit and the electrode pad can also be directly connected without wires;
wherein the unit and the electrode pad are electrically connected to each other through the conductive connector and Ultrasound therapy head;
wherein the conductive connector and the Ultrasound therapy head are on the electrode pad and/or the unit;
wherein the unit includes batteries and function keys;
wherein the batteries are rechargeable batteries or non-rechargeable batteries;
wherein the function keys include power on/off key, Ultrasound key, and TENS/EMS key.

8. The system of claim 7, further comprising:
wherein the Ultrasound therapy head and the TENS/EMS electrode can be attached in the same electrode pad;
wherein the electrode pad includes the Ultrasound therapy head, conductive connector, non-conductive layer, conductive layer, and sticky gel.

9. The system of claim 7, further comprising:
wherein the Ultrasound therapy head and the TENS/EMS electrode can also be in two independent electrode pads;
wherein a first electrode pad includes Ultrasound therapy head;
wherein a second electrode pad includes conductive connector, non-conductive layer, conductive layer, and sticky gel.

10. The system of claim 7, further comprising:
wherein the IC board also includes a temperature adjustment module, and the electrode pad also includes a heating layer;
wherein the temperature adjustment module is electrically connected to the heating layer of the electrode pad;
wherein the heating layer is set between the non-conductive layer and conductive TENS/EMS layer.

11. The system of claim 10, further comprising:
wherein the board also includes a signal receiving/transmitting module;
wherein the unit can be remotely operated through the signal receiving/transmitting module by Bluetooth, radio waves, or WIFI.

12. A system of a portable Ultrasound and TENS/EMS electronic pulse stimulator including a unit and an electrode pad;
wherein the unit and the electrode pad are electrically connected to each other by a lead wire or without wires, characterized in that the unit includes an IC board and a housing;
wherein the IC board has an Ultrasound output module and a TENS/EMS module;
wherein the electrode pad has an Ultrasound therapy head and a TENS/EMS electrode;
wherein the unit and the electrode pad can be electrically connected by a lead wire;
wherein one end of the lead wire combines the ultrasound head and the conductive connector of the electrode pad and/or the lead wire;
wherein the other end of the wire is connected to the output port of the IC board;
wherein the unit and the electrode pad can also be directly connected without wires;
wherein the unit and the electrode pad are electrically connected to each other through the conductive connector and Ultrasound therapy head;
wherein the conductive connector and the Ultrasound therapy head are on the electrode pad and/or the unit;
wherein the Ultrasound therapy head and the TENS/EMS electrode can be attached in the same electrode pad or in two independent, electrode pads;
wherein the unit includes batteries and function keys;
wherein the batteries are rechargeable batteries or non-rechargeable batteries;
wherein the function keys include power on/off key, Ultrasound key, and TENS/EMS key.

* * * * *